United States Patent [19]

Allen et al.

[11] 4,212,194
[45] Jul. 15, 1980

[54] MEASUREMENT OF EQUILIBRIUM RELATIVE HUMIDITY

[75] Inventors: Donald C. Allen; Alan T. Smith, both of Sittingbourne, United Kingdom

[73] Assignee: EPS (Research & Development) Limited, Sittingbourne, England

[21] Appl. No.: 47,736

[22] Filed: Jun. 12, 1979

[30] Foreign Application Priority Data

Aug. 11, 1978 [GB] United Kingdom ............ 33083/78

[51] Int. Cl.² .................. G01N 27/46; G01N 33/02
[52] U.S. Cl. ............................................................ 73/73
[58] Field of Search .................. 73/73, 76, 29, 19; 204/17, 195 W

[56] References Cited

U.S. PATENT DOCUMENTS

| | | | |
|---|---|---|---|
| 1,014,842 | 1/1912 | Muckenfuss | 73/73 X |
| 2,834,201 | 5/1958 | Ohlheiser | 73/73 |
| 4,050,995 | 9/1977 | Bredeweg | 204/195 W X |

*Primary Examiner*—James J. Gill
*Attorney, Agent, or Firm*—Parmelee, Miller, Welsh & Kratz

[57] ABSTRACT

The equilibrium relative humidity over a substance may be determined by the following method. The sample of the substance is placed in a lower compartment of a diffusion chamber and a dried gas is then passed through an upper compartment of the chamber which is partitioned from the lower by a disc of water vapor permeable non-hygroscopic material. When the rate of diffusion of water vapor through the disc from the lower to the upper compartment becomes constant the equilibrium relative humidity of the sample is directly related to the moisture concentration in the sweep gas and can be readily determined from a suitable calibration graph for the disc.

9 Claims, 3 Drawing Figures

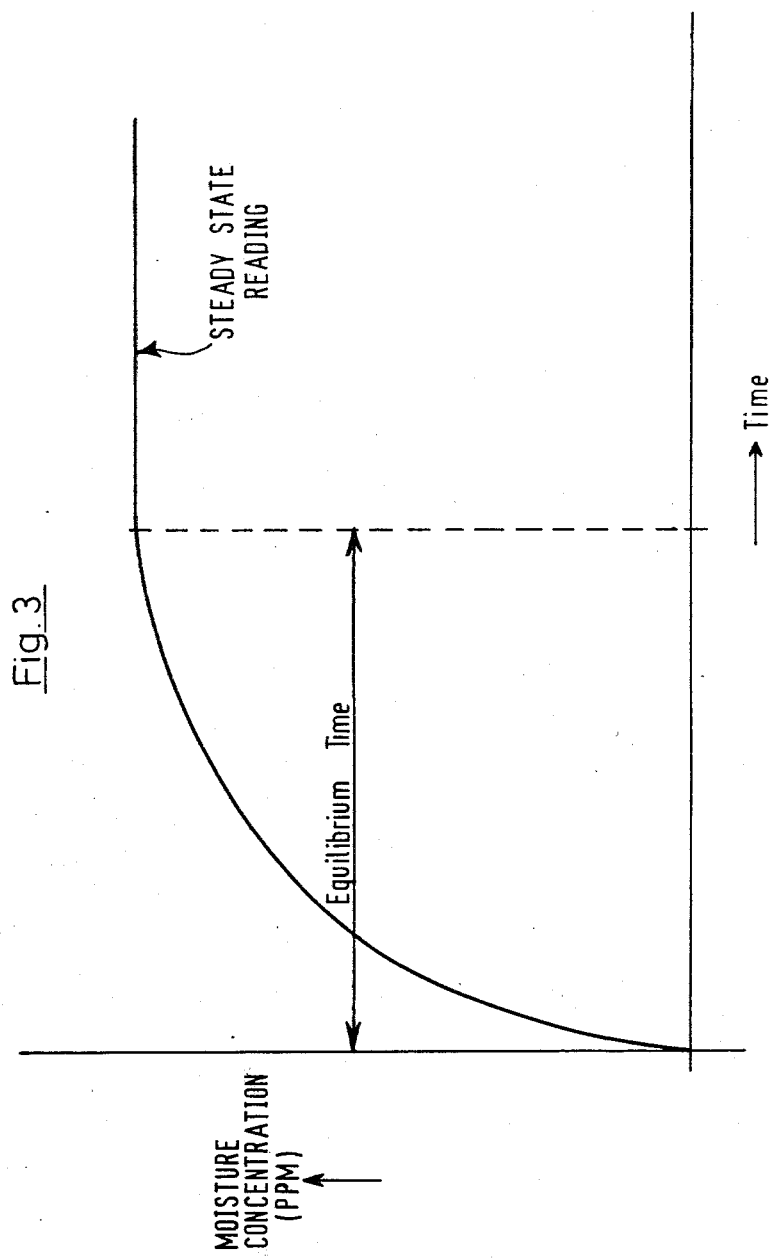

MEASUREMENT OF EQUILIBRIUM RELATIVE HUMIDITY

This invention relates to a method of effecting measurements of equilibrium relative humidity. In particular the invention relates to the measurement of equilibrium relative humidity over solid or liquid test specimens.

The measurement of equilibrium relative humidity over various substances is of great interest to the food industry, since the equilibrium relative humidity over a substance is an indicator of its moisture content which must be carefully controlled both during manufacture and subsequently in the food package if the quality of the food is satisfactorily to be maintained.

This invention seeks to provide an improved method of determining the equilibrium relative humidity of various test substances.

According to this invention there is provided a method for determining the equilibrium relative humidity over a substance, the method comprising the steps of placing a sample of the substance in a first compartment of a diffusion chamber, said first compartment being partitioned from a second compartment of said chamber by means of a water vapour permeable non-hygroscopic material and said second compartment being provided with inlet and outlet ports, sweeping a dried gas at a constant rate through said second compartment via said inlet and outlet ports, and determining the moisture concentration in the outgoing gas when steady state diffusion conditions have been established and determining, from said moisture concentration, the equilibrium relative humidity over the sample.

Preferably the moisture concentration in the gas is determined by passing said gas from said second compartment through a measuring electrolytic cell and measuring the current drawn by said electrolytic cell when a condition of steady state diffusion is reached, thereby to determine the moisture concentration in the gas.

The moisture concentration in the outgoing gas when the apparatus is operated under predetermined conditions is substantially linearly related to said equilibrium relative humidity and it is thus possible to produce a calibrated scale or chart to enable the equilibrium relative humidity over said sample to be measured directly from the moisture concentration value when the apparatus is operated under the predetermined conditions.

Advantageously the permeable non-hygroscopic material has a very high permeability to water vapour and reaches steady state diffusion conditions very quickly. Conveniently the material is a sheet of plastics material or a sheet of finely perforated metal and preferably the sheet material is silicone rubber.

Preferably the diffusion chamber and the measuring electrolytic cell are positioned in a temperature controlled enclosure.

Conveniently, prior to being swept through the second compartment of the diffusion chamber, the gas is dried by being passed through a drying electrolytic cell. Advantageously the gas is nitrogen.

In order that the invention may be more readily understood and so that further features thereof may be appreciated the invention will now be described by way of example and with reference to the accompanying drawings in which:

FIG. 3 is a graph illustrating the relationship between the moisture concentration detected in a gas passed through an apparatus as shown in FIG. 1 and time.

Figure 1:
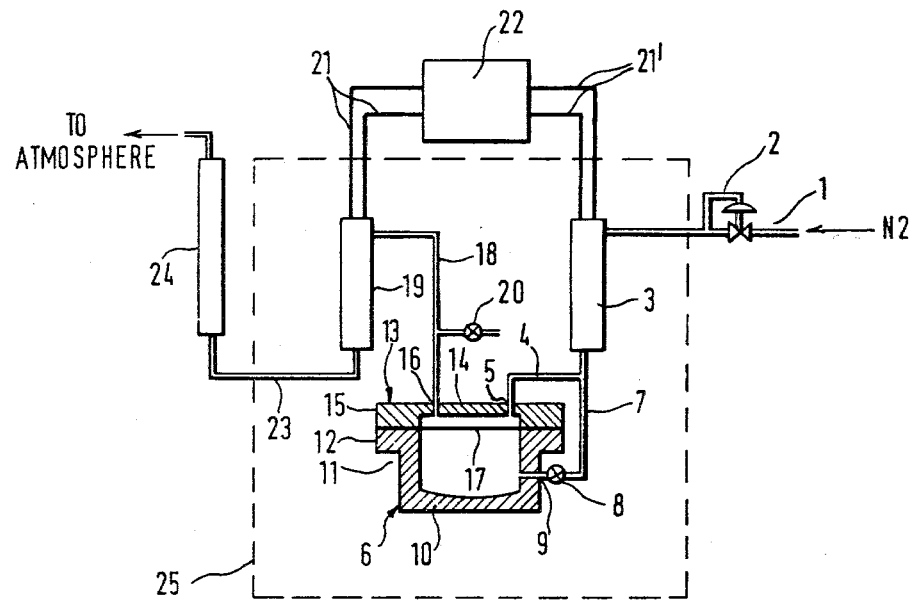
FIG. 1 is a schematic diagram of apparatus for determining the equilibrium relative humidity over a substance by a method in accordance with the invention.

Referring to FIG. 1 of the drawings, an apparatus for determining the equilibrium humidity over a substance is shown, the apparatus being used in this case to determine the equilibrium relative humidity over a solid substance. The apparatus comprises conduit 1 adapted to be connected to a source of nitrogen and having a flow control valve 2. The conduit 1 leads to a drying electrolytic cell 3 which comprises two platinum or rhodium wires wound onto an insulating tube without contacting each other, there being a film of phosphorus pentoxide deposited over and between the wires. A potential difference is maintained across the wires and as the phosphorus pentoxide, which is virtually non-conductive when dry, absorbs water it becomes conductive and current flows between the two wires electrolysing the absorbed water to hydrogen and oxygen. In this way the nitrogen which flows past the wires is dried, since all the water vapour in the gas is converted to hydrogen and oxygen.

A second conduit 4 leads from the drying electrolytic cell to an inlet port 5 of a diffusion chamber 6. A branch conduit 7 extends from the second conduit 4 via a valve 8 which is normally in a closed position to another inlet port 9 of the diffusion chamber 6.

The lower part of the diffusion chamber comprises a sample containing compartment having a bottom wall 10 a peripheral upwardly extending side wall 11 and a flange 12 extending radially outwardly from the upper edge of the side wall 11. The inlet port 9 previously mentioned opens through the side wall 11.

The upper part of the diffusion chamber forms a lid 13 which comprises a top wall 14 and a peripheral annular raised portion 15 which defines an upper compartment. The inlet port 5 mentioned above extends through said top wall 14 to communicate with the upper compartment. An outlet port 16 also extends through the top wall 14 to communicate with the upper compartment. Nitrogen from the drying cell can thus be flushed through the upper compartment formed by the lid 13.

The annular portion 15 of the lid 13 is arranged to be clamped to the flange 12 of the lower part of the diffusion chamber to trap a disc of water vapour permeable non-hygroscopic material 17 in position. The disc 17 serves as a partition between the upper and lower compartments. The disc 17 is made from a material with a very high permeability to water vapour which will reach a condition of steady state diffusion in a very short time. In this embodiment of the invention the sheet comprises a disc of silicone rubber.

An outlet conduit 18 for nitrogen flushed through the upper compartment extends from the outlet port 16 to a measuring electrolytic cell 19. A by-pass valve 20 is provided in the conduit 18 to enable the nitrogen to be vented directly to the atmosphere when desired.

The measuring electrolytic cell 19 is identical to the drying electrolytic cell 3. A potential difference is applied across the electrodes of the measuring cell and as water vapour carried into the cell by the nitrogen is electrolysed the current is measured to determine, by application of Faraday's Law of Electrolysis, the amount of water absorbed by the phosphorus pentoxide deposited over the wires forming the electrode. Leads 21 from the measuring electrolytic cell 19 and leads 21' from the drying electrolytic cell 3 are connected to an electrolytic hygrometer 22, which includes a microammeter to measure the current flowing in the measuring electrolytic cell 19, and also in the drying electrolytic cell 3 if desired, the current being proportional to the quantity of water electrolised at any instant.

An outlet conduit 23 leads from the measuring electrolytic cell to a flow meter 24 which is used to monitor nitrogen flow before discharging to the atmosphere.

A controlled temperature enclosure 25 is provided to maintain the electrolytic cells 3, 19 and the diffusion chamber, together with the conduits interconnecting these components, at a constant predetermined temperature.

In order to determine the equilibrium relative humidity over a substance, a sample of the substance is introduced to the lower compartment of the diffusion chamber 6 and the silicone rubber disc 17 is clamped in position between the lid 13 and the sample containing compartment of the diffusion chamber 6.

Nitrogen is passed at a constant rate through the conduit 1 to the drying electrolytic cell 3. A potential difference is applied across the electrodes of the electrolytic cell 3 to dry the nitrogen before it passes along the conduit 4 and into the upper compartment of the diffusion chamber. Water vapour from the sample mixes with the air in the space in the lower compartment between the silicone rubber disc 17 and the surface of the sample. Some of the water vapour passes through the silicone rubber disc to the upper compartment of the diffusion chamber where it is swept away by the nitrogen passing into the chamber from the conduit 4 and subsequently passes out of the chamber via the conduit 18, to the measuring electrolytic cell 19. A potential difference is applied across the electrodes of the cell 19 and the water vapour present in the nitrogen is absorbed by the phosphorous pentoxide coating over the electrodes. A current flow between the electrodes electrolyses the water absorbed by the phosphorus pentoxide and this current is measured by means of the microammeter in the electrolytic hygrometer 22. After passing through the measuring electrolytic cell the nitrogen passes through a flow meter which monitors the flow of nitrogen through the apparatus and subsequently the nitrogen is discharged into the atmosphere. The two electrolytic cells, the diffusion chamber and the associated communicating conduits are maintained at a constant temperature in the controlled temperature enclosure 25.

The amount of water vapour passing through the disc 17 increases with time in a roughly exponential manner (FIG. 3) until steady state diffusion conditions are established. This becomes apparent when the current drawn by the measuring electrolytic cell reaches a constant value. The magnitude of the current flowing through the measuring electrolytic cell is directly related by Faraday's Law of Electrolysis to the mass flow of water vapour into the electrolytic cell 19. Thus at a constant nitrogen flow rate the moisture concentration in the nitrogen can be determined directly from the current value measured by the microammeter, which has a scale calibrated in parts per million of moisture.

It has been shown that for a particular temperature the moisture concentration in the gas passing through the upper compartment is linearly related to the equilibrium relative humidity over the substance under test. Thus it is a simple matter once the silicone rubber disc 17 has been calibrated, to determine the equilibrium relative humidity of any substance in the lower compartment.

Figure 2:
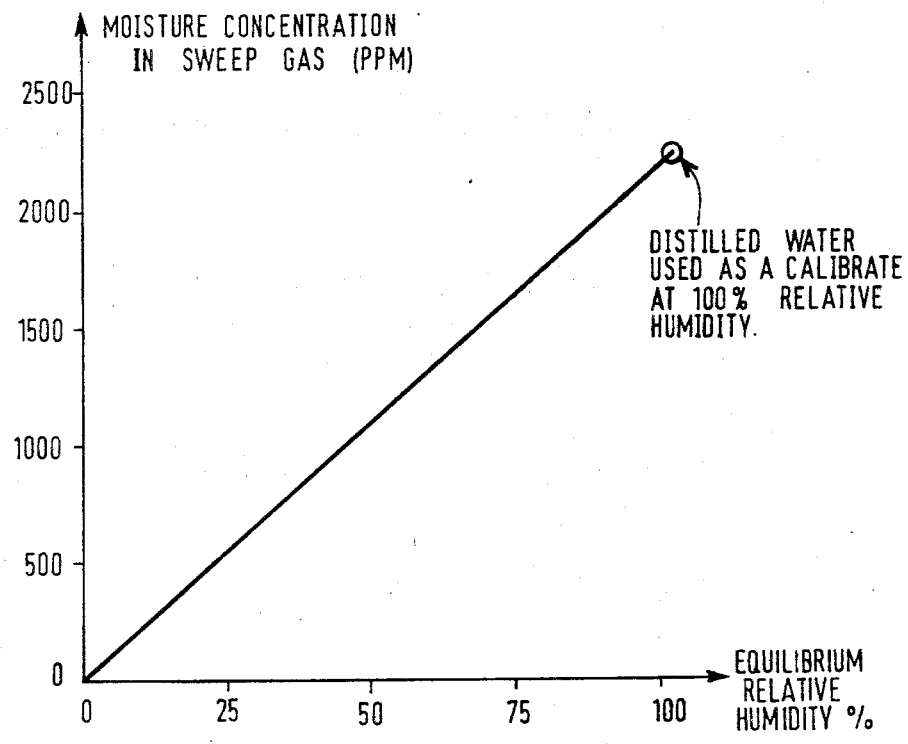
FIG. 2 is a graph representing the relationship between the equilibrium relative humidity over a substance and the moisture concentration detected in a gas passed through an apparatus as shown in FIG. 1 under standard conditions.

FIG. 2 shows a calibration graph for one type of silicone rubber suitable for the equilibrium relative humidity range from 0 to 100%. The slope of the line is determined by measuring the moisture concentration in the nitrogen for a number of calibrating substances which have known values of equilibrium relative humidity (standard solutions). FIG. 2 relates to James Walker silicone rubber of a thickness of 0.030 inches at a temperature of 25° C. It will be appreciated that once the moisture concentration in the nitrogen has been determined for a sample substance, at a temperature of 25° C, and using such a silicone rubber disc, it is a simple matter to determine from the graph the equilibrium relative humidity of the test substance.

Conveniently the electrolytic hygrometer 22 may be provided with a pen recorder to indicate directly when steady state diffusion conditions in the silicone rubber disc 17 have been reached.

It should be mentioned briefly that the branch conduit 7 and the associated valve 8 are provided to enable the lower compartment of the diffusion chamber to be dried down when desired. Similarly the bypass valve 20 is provided to enable the upper compartment to be dried down. This procedure is used to check the instrument for leaks.

Whilst the invention has been described with reference to the measurement of the equilibrium relative humidity over a solid sample, the method of the invention may be used for the measurement of the equilibrium relative humidity over a sample of a liquid material, or over a sample of a gel or other material.

It will be appreciated that the disc 17 could be formed of materials other than silicone rubber, such as for example, a sheet of plastics material or a sheet of finely perforated metal.

We claim:

1. A method for determining the equilibrium relative humidity over a substance, the method comprising the steps of placing a sample of the substance in a first compartment of a diffusion chamber, said first compartment being partitioned from a second compartment of said chamber by means of water vapour permeable non-hygroscopic material and said second compartment being provided with inlet and outlet ports, sweeping a dried gas at a constant rate through said second compartment via said inlet and outlet ports, and determining the moisture concentration in the gas when conditions of steady state diffusion have been reached, and calculating from said moisture concentration, the equilibrium relative humidity over the sample.

2. A method according to claim 1, wherein the moisture concentration in the gas is determined by passing said gas from said second compartment through a measuring electrolytic cell and measuring the current drawn by said electrolytic cell at steady state diffusion conditions, thereby to determine the moisture concentration in the gas.

3. A method according to claim 1 or claim 2, wherein the permeable non-hygroscopic material has a very high permeability to water vapour and has a short time to steady state diffusion conditions.

4. A method according to claim 3, wherein the material is a sheet of plastics material.

5. A method according to claim 3, wherein the material is a sheet of finely perforated metal.

6. A method according to claim 3, wherein the material is a sheet of silicone rubber.

7. A method according to claim 1 wherein at least the diffusion chamber is positioned in a temperature controlled enclosure.

8. A method according to claim 1 wherein, prior to being swept through the second compartment of the diffusion chamber, the gas is dried by being passed through a drying electrolytic cell.

9. A method according to claim 1 wherein the gas is nitrogen.

* * * * *